US009207072B2

(12) United States Patent
Serizawa

(10) Patent No.: US 9,207,072 B2
(45) Date of Patent: *Dec. 8, 2015

(54) LEAF AREA INDEX MEASUREMENT SYSTEM, DEVICE, METHOD, AND PROGRAM

(75) Inventor: Masahiro Serizawa, Minato-ku (JP)

(73) Assignee: NEC CORPORATION, Tokyo (JP)

( * ) Notice: Subject to any disclaimer, the term of this patent is extended or adjusted under 35 U.S.C. 154(b) by 424 days.

This patent is subject to a terminal disclaimer.

(21) Appl. No.: 13/883,494

(22) PCT Filed: Dec. 2, 2011

(86) PCT No.: PCT/JP2011/006764
§ 371 (c)(1),
(2), (4) Date: May 3, 2013

(87) PCT Pub. No.: WO2012/073520
PCT Pub. Date: Jun. 7, 2012

(65) Prior Publication Data
US 2013/0235190 A1  Sep. 12, 2013

(30) Foreign Application Priority Data

Dec. 2, 2010  (JP) .................................. 2010-269719

(51) Int. Cl.
| G06K 9/00 | (2006.01) |
| G01B 11/28 | (2006.01) |
| A01G 7/00 | (2006.01) |
| G01N 21/84 | (2006.01) |

(52) U.S. Cl.
CPC ............... *G01B 11/285* (2013.01); *A01G 7/00* (2013.01); *G01N 21/84* (2013.01); *G01N 2021/8466* (2013.01)

(58) Field of Classification Search
None
See application file for complete search history.

(56) References Cited

U.S. PATENT DOCUMENTS 8,352,208 B2 *  1/2013  Yamamoto ............. A01G 23/00
356/629
2009/0281733 A1 *  11/2009  Yamamoto ........... H04N 5/2254
702/19

(Continued)

FOREIGN PATENT DOCUMENTS

| CN | 101330823 A | 12/2008 |
| CN | 101413875 A | 4/2009 |

(Continued)

OTHER PUBLICATIONS

Communication dated May 22, 2015 from the State Intellectual Property Office of the P.R.C. in counterpart application No. 201180057953.6

(Continued)

*Primary Examiner* — Nancy Bitar
(74) *Attorney, Agent, or Firm* — Sughrue Mion, PLLC

(57) ABSTRACT

A leaf area index measurement system includes: imaging means for capturing an image of a measurement target plant and outputting the captured image; a light source placed either on a side of the measurement target plant opposite to the imaging means or at a position of the measurement target plant; intensity calculation means for calculating an intensity of light when the light source emits light, based on the captured image output from the imaging means; and leaf area index calculation means for calculating a leaf area index, based on the intensity of light calculated by the intensity calculation means.

8 Claims, 3 Drawing Sheets

(56) References Cited

U.S. PATENT DOCUMENTS

| | | | | |
|---|---|---|---|---|
| 2013/0182911 | A1* | 7/2013 | Tsukada | ............... A01G 7/00 382/110 |
| 2013/0301892 | A1* | 11/2013 | Liu | ............... A61B 5/0033 382/131 |

FOREIGN PATENT DOCUMENTS

| | | |
|---|---|---|
| CN | 101539409 A | 9/2009 |
| CN | 101852598 A | 10/2010 |
| JP | 8-247746 A | 9/1996 |
| JP | 03-143961 A | 5/2003 |
| JP | 2004-3878 A | 1/2004 |
| JP | 2005-052045 A | 3/2005 |
| JP | 2007-171033 A | 7/2007 |
| JP | 2008-111725 A | 5/2008 |
| WO | 2007/069736 A1 | 6/2007 |

OTHER PUBLICATIONS

Communication dated May 22, 2015 from the State Intellectual Property Office of the P.R.C. in counterpart application No. 201180057953.6.

Communication dated Aug. 27, 2014 from the State Intellectual Property Office of People's Republic of China in counterpart application No. 201180057953.6.

* cited by examiner

FIG. 5

| RANGE OF EV VALUE | LAI |
|---|---|
| $A(1) \leq EV < A(2)$ | $L(1)$ |
| $A(2) \leq EV < A(3)$ | $L(2)$ |
| ⋮ | ⋮ |
| $A(N) \leq EV \leq A(N+1)$ | $L(N)$ |

LEAF AREA INDEX MEASUREMENT SYSTEM, DEVICE, METHOD, AND PROGRAM

This is a National Stage Entry of Application No. PCT/JP2011/006764 filed Dec. 2, 2011, claiming priority based on Japanese Patent Application No. 2010-269719 filed Dec. 2, 2010, the contents of all of which are incorporated herein by reference in their entirety.

TECHNICAL FIELD

The present invention relates to a leaf area index measurement system, a leaf area index measurement device, a leaf area index measurement method, and a leaf area index measurement program for measuring a leaf area index.

BACKGROUND ART

A leaf area index (hereafter "LAI") represents a total area of leaves overlapping in a direction (e.g. a vertical direction) per unit area in, for example, a plant community in agricultural land or forests. The LAI is used as one index for understanding plant growth or cultivation states.

As an LAI measurement method, a method of indirectly measuring the LAI using an illuminometer is proposed as an example. In this method, for instance, illuminance is measured above and below in a plant community, and the LAI is estimated based on the measured illuminance.

As a technique related to this, for instance, an LAI indirect measurement method is described in Patent Literature (PTL) 1.

In the method described in PTL 1, an indirect measurement system captures an image of a predetermined area for each of near-infrared light and red light, using a wide angle lens and an electronic imaging element. Next, the indirect measurement system obtains a luminance value for each of near-infrared light and red light, in each subdivision area formed by dividing the predetermined area. The indirect measurement system then calculates a luminance value ratio of near-infrared light and red light for each subdivision area, estimates a relative amount of solar radiation based on the luminance value ratio, and calculates the LAI from the relative amount of solar radiation.

CITATION LIST

Patent Literature(s)

PTL 1: Japanese Patent Application Laid-Open No. 2007-171033

SUMMARY OF INVENTION

Technical Problem

However, in the case of indirectly measuring the LAI using the illuminometer, an expensive illuminometer is necessary and also the measurement needs to be performed a plurality of times while moving the illuminometer, in order to determine the LAI in each of a plurality of locations in a community structure. Thus, a great deal of labor and cost are required.

The method described in PTL 1 achieves a certain degree of cost reduction by using the electronic imaging element in the indirect measurement system instead of the illuminometer. However, since sunlight is used, it is impossible to freely control an irradiation direction of light from the light source, posing a limit to directions in which the relative amount of solar radiation can be measured. Thus, locations or directions in which the LAI can be measured are limited in the method described in PTL 1.

In view of this, the present invention has an object of providing a leaf area index measurement system, a leaf area index measurement device, a leaf area index measurement method, and a leaf area index measurement program capable of automatically measuring a leaf area index easily at low cost, without a limit to measurement locations or directions.

Solution to Problem

A leaf area index measurement system according to the present invention includes: imaging means for capturing an image of a measurement target plant and outputting the captured image; a light source placed either on a side of the measurement target plant opposite to the imaging means or at a position of the measurement target plant; intensity calculation means for calculating an intensity of light when the light source emits light, based on the captured image output from the imaging means; and leaf area index calculation means for calculating a leaf area index, based on the intensity of light calculated by the intensity calculation means.

A leaf area index measurement device according to the present invention is a leaf area index measurement device for measuring a leaf area index in a leaf area index measurement system that includes: imaging means for capturing an image of a measurement target plant and outputting the captured image; and a light source placed either on a side of the measurement target plant opposite to the imaging means or at a position of the measurement target plant, the leaf area index measurement device including: intensity calculation means for calculating an intensity of light when the light source emits light, based on the captured image output from the imaging means; and leaf area index calculation means for calculating a leaf area index, based on the intensity of light calculated by the intensity calculation means.

A leaf area index measurement method according to the present invention includes: providing imaging means for capturing an image of a measurement target plant and outputting the captured image; providing a light source placed either on a side of the measurement target plant opposite to the imaging means or at a position of the measurement target plant; calculating an intensity of light when the light source emits light, based on the captured image output from the imaging means; and calculating a leaf area index, based on the calculated intensity of light.

A leaf area index measurement program according to the present invention is a leaf area index measurement program for measuring a leaf area index in a leaf area index measurement system that includes: imaging means for capturing an image of a measurement target plant and outputting the captured image; and a light source placed either on a side of the measurement target plant opposite to the imaging means or at a position of the measurement target plant, the leaf area index measurement program causing a computer to execute: an intensity calculation process of calculating an intensity of light when the light source emits light, based on the captured image output from the imaging means; and a leaf area index calculation process of calculating a leaf area index, based on the calculated intensity of light.

Advantageous Effects of Invention

According to the present invention, it is possible to automatically measure a leaf area index easily at low cost, without a limit to measurement locations or directions.

BRIEF DESCRIPTION OF DRAWINGS

FIG. 5 is an explanatory diagram showing an example of a table for transforming an EV value to an LAI.

DESCRIPTION OF EMBODIMENT(S)

Figure 1:
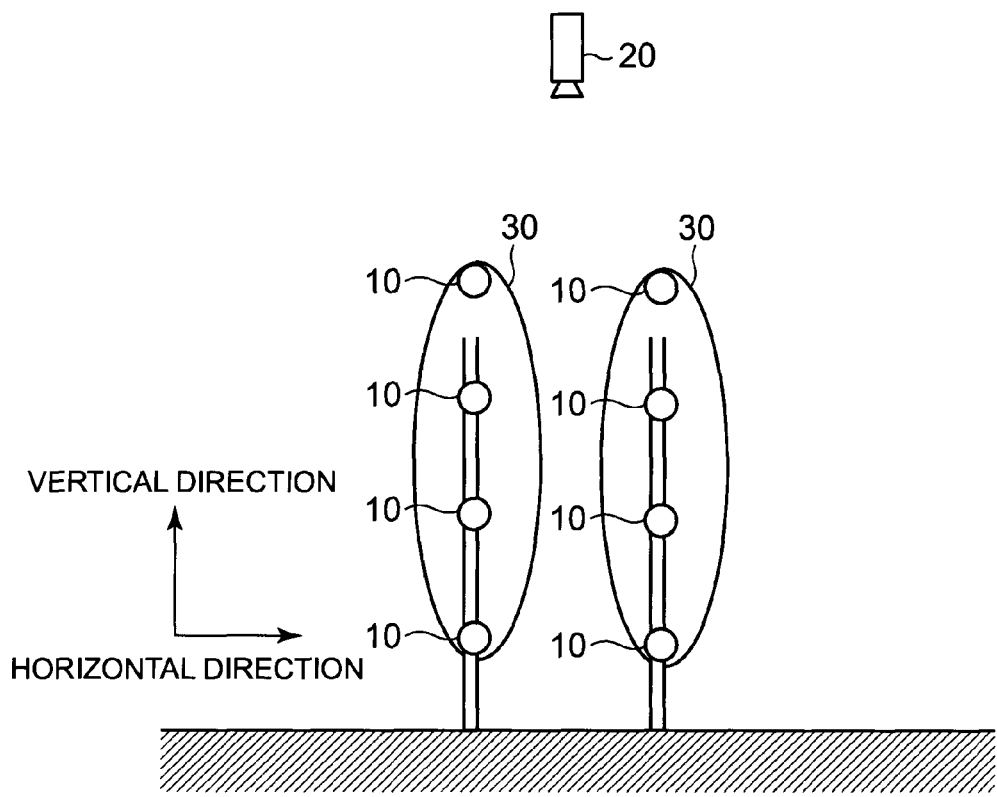
FIG. 1 is a front view of a measurement system using an LAI measurement system according to the present invention, as seen from front with respect to a plant community.

An embodiment of the present invention is described below, with reference to drawings. FIG. 1 is a front view of a measurement system using an LAI measurement system (leaf area index measurement system) according to the present invention, as seen from front with respect to a plant community. In this exemplary embodiment, it is assumed that a plant community 30 is a plant group in which plants for agricultural crops are arranged in line, as shown in FIG. 1. Though FIG. 1 shows a sectional view taken along a section of the plant community 30, the plant community 30 is a plant group in which plants are arranged in line in a depth direction (a direction from front to back of the plant community 30 as seen in FIG. 1, hereafter also referred to as "longitudinal direction").

As shown in FIG. 1, in this exemplary embodiment, the expressions such as "vertical direction" and "horizontal direction" are used, too. The "vertical direction" represents a direction vertical to the ground, and the "horizontal direction" represents a direction horizontal to the ground, as shown in FIG. 1.

Though this exemplary embodiment describes, as an example, the case where the LAI measurement system is applied to measurement of an LAI in a plant community for agricultural crops (e.g. tomatoes, cucumbers) in agricultural land such as a field or a plastic greenhouse, the present invention is not limited to the example in this exemplary embodiment. The LAI measurement system may be applied to, for instance, measurement of an LAI in a tree group in forests.

As shown in FIG. 1, in this exemplary embodiment, a plurality of light sources 10 are arranged in the plant community 30, and a camera 20 for capturing an image of the plant community 30 is placed above the plant community 30.

The light sources 10 are each specifically realized by a lamp or an LED capable of producing light of a predetermined wavelength. Though eight light sources 10 are arranged in the example shown in FIG. 1 (four light sources 10 are arranged in the vertical direction per plant community 30 as shown in FIG. 1), the number of light sources 10 that can be arranged is not limited to the example in this exemplary embodiment. For instance, only one light source 10 may be arranged, and ten or more light sources 10 may be arranged (five or more light sources 10 may be arranged in the vertical direction per plant community 30).

The camera 20 is specifically realized by an imaging device such as a digital camera capable of capturing monochrome images or color images. The camera 20 is not limited to a camera for capturing still images and may be realized, for example, by a video camera capable of capturing moving images, as long as it is capable of capturing monochrome images or color images. As shown in FIG. 1, the camera 20 has a function of capturing an image in the direction of the plant community 30 and outputting the captured image to a below-mentioned LAI measurement device 40 (not shown in FIG. 1). In this exemplary embodiment, the camera 20 is placed above the plant community 30 to measure the LAI in the vertical direction as shown in FIG. 1, in order to recognize the overlapping state of leaves in the plant community 30 when seen in the vertical direction.

Though FIG. 1 shows the example of placing one camera 20, the number of cameras 20 placed is not limited to the example in this exemplary embodiment. For instance, two or more cameras 20 may be placed. That is, at least one camera 20 is placed to be able to capture the image in the direction of the plant community 30.

In this exemplary embodiment, the camera 20 is placed substantially directly above the plant community 30 in order to measure the LAI in the vertical direction, as shown in FIG. 1. However, the position of the camera 20 is not limited to the example in this exemplary embodiment. The camera 20 may be placed diagonally above the plant community 30, as long as the camera 20 is at such a position that enables the measurement of the LAI in the vertical direction. In the case of placing the camera 20 in this way, each light source 10 may be placed not in the plant community 30 but at a position that is on the side of the plant community 30 opposite to the camera 20 and is slightly shifted from the plant community 30 (i.e. placed in such a positional relationship in which the plant community 30 is sandwiched between each light source 10 and the camera 20). That is, the placement is made so as to ensure a difference in height between each light source 10 and the camera 20 to enable the measurement of the LAI in the vertical direction.

Though FIG. 1 shows the example where four light sources 10 are arranged in the vertical direction in one location in the plant community 30 to perform the measurement, a group of four light sources 10 in the vertical direction may equally be placed at predetermined intervals (e.g. intervals of 50 cm) in the longitudinal direction in the plant community 30 (i.e. light sources are arranged in a lattice when seen from a longitudinal side) to perform the measurement. This enables the LAI measurement system to also measure an LAI distribution in the longitudinal direction of the plant community 30.

Moreover, the camera 20 may be placed so as to capture the image of the plant community 30 in the horizontal direction, in order to measure not the LAI in the vertical direction but the LAI in the horizontal direction. In this case, instead of placing the plurality of light sources 10 in the plant community 30, the light sources 10 may be placed on one side of the plant community 30, with the camera 20 being placed on the opposite side of the plant community 30 to the light sources 10 so as to sandwich the plant community 30.

Figure 2:
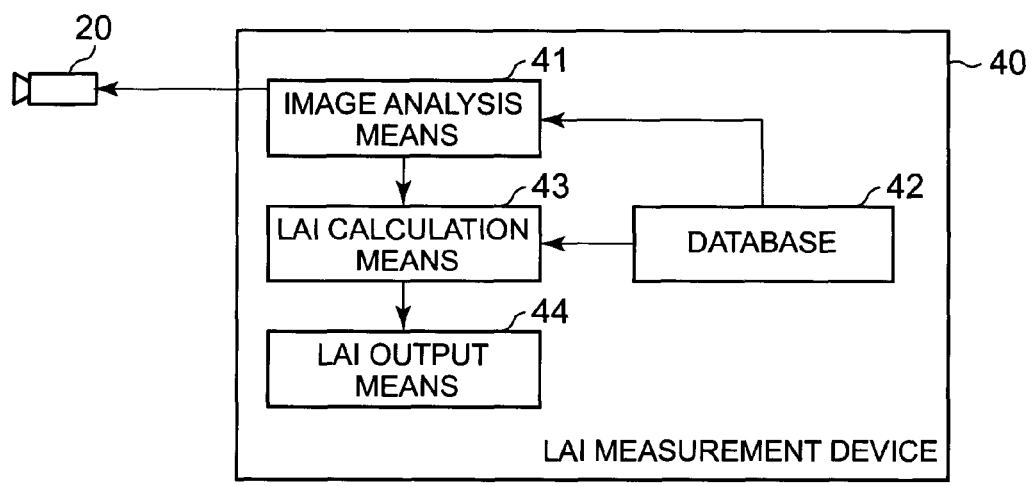
FIG. 2 is a block diagram showing an example of a structure of the LAI measurement system.

FIG. 2 is a block diagram showing an example of a structure of the LAI measurement system. As shown in FIG. 2, the LAI measurement system includes the LAI measurement device 40, in addition to the camera 20 for capturing the image of the light sources 10 shown in FIG. 1. The captured image is output from the camera 20 to the LAI measurement device 40, as shown in FIG. 2. The LAI measurement device 40 is specifically realized by an information processing device such as a personal computer operating according to a program. As shown in FIG. 2, the LAI measurement device 40 includes image analysis means 41, a database 42, LAI calculation means 43, and LAI output means 44.

The image analysis means 41 is specifically realized by a CPU of the information processing device operating according to the program. The image analysis means 41 has a function of calculating a luminance value of the captured image received from the camera 20. Here, the image analysis means 41 may calculate a luminance value of the whole captured image received from the camera 20, or extract a partial image from the whole captured image received from the camera 20 and calculate a luminance value of the extracted partial image. For example, the image analysis means 41 may specify, in the captured image, a part in which a light source 10 emitting light is shown, extract a partial image including the specified part, and calculate a luminance value of the extracted partial image. In this exemplary embodiment, the light sources 10 are caused to emit light in sequence, and the image analysis means 41 calculates an intensity of light (e.g. luminance or illuminance) leaking from the plant community 30.

The image analysis means 41 also has a function of transforming the calculated luminance value to illuminance. In this exemplary embodiment, the image analysis means 41 calculates the illuminance by extracting, from an illuminance transformation table stored in the below-mentioned database 42, the illuminance corresponding to the luminance value calculated by the image analysis means 41.

The database 42 is specifically realized by a storage device such as a magnetic disk device or an optical disk device. In this exemplary embodiment, the database 42 stores the illuminance transformation table for transforming the luminance value to the illuminance. In detail, the illuminance transformation table stored in the database 42 includes the luminance value and the illuminance in association with each other. For example, the illuminance transformation table stored in the database 42 is created by, under several conditions as samples, setting illuminance measured using a commonly used illuminometer and a luminance value obtained from a captured image beforehand.

The database 42 also stores an LAI transformation table for transforming the illuminance to the LAI. In detail, the LAI transformation table stored in the database 42 includes the illuminance and the LAI in association with each other. For example, the LAI transformation table stored in the database 42 is created by, under several conditions as samples, setting illuminance measured using a commonly used illuminometer and an LAI calculated at the time beforehand.

The LAI calculation means 43 is specifically realized by the CPU of the information processing device operating according to the program. The LAI calculation means 43 has a function of calculating the LAI based on the illuminance calculated by the image analysis means 41. In detail, the LAI calculation means 43 calculates the LAI by extracting, from the LAI transformation table stored in the database 42, the LAI corresponding to the illuminance calculated by the image analysis means 41.

The method of calculating the leaf area index is not limited to the above-mentioned method. As an example, the following method may be employed to calculate the leaf area index.

For instance, one or more light sources are caused to emit light, and an image sensor (e.g. the camera 20) whose aperture value and shutter speed are automatically set captures the image. Then, the LAI calculation means 43 calculates the leaf area index using a table created beforehand, from an exposure value (EV value) determined using the set aperture value and shutter speed.

An example of the method of calculating the EV value is described below. The EV value is determined using a sum $A_V + T_V$ of an $A_V$ value and a $T_V$ value which are respectively calculated from an aperture value N and a shutter speed t according to the following equations.

$$AV = \log_2 N^2 = 2\log_2 N \qquad \text{Equation (1).}$$

$$TV = \log_2 1/t = -\log_2 t \qquad \text{Equation (2).}$$

An example of the method of creating the table for transforming the EV value to the LAI is described below. First, a large number of pairs of EV values measured by the method in the present application and LAIs measured and calculated using a conventional method in the same state are collected. Next, the table is created by calculating an LAI mean value (L(i) where i=1, ..., N) for each specific EV value section (A(i) to A(i+1) where i=1, ..., N) as in a table shown in FIG. 5, using the collected EV values and LAIs. Here, actual figures are assigned to A(1) to A(N+1) and L(1) to L(N).

The LAI output means 44 is specifically realized by the CPU of the information processing device operating according to the program and a display device such as a display. The LAI output means 44 has a function of outputting the LAI calculated by the LAI calculation means 43. For example, the LAI output means 44 displays the LAI calculated by the LAI calculation means 43, on the display device such as the display. The method of outputting the LAI is not limited to the example in this exemplary embodiment. As an example, the LAI output means 44 may output a file including the LAI calculated by the LAI calculation means 43. As another example, the LAI output means 44 may transmit the LAI calculated by the LAI calculation means 43, to another terminal via a network such as a LAN.

In this exemplary embodiment, the storage device of the LAI measurement device 40 stores various programs for measuring the LAI. For instance, the storage device of the LAI measurement device 40 stores an LAI (leaf area index) measurement program for causing a computer to execute: a process of calculating an intensity of light when the light source 10 emits light, based on a captured image output from imaging means; and a process of calculating a leaf area index based on the calculated intensity of light.

Figure 3:
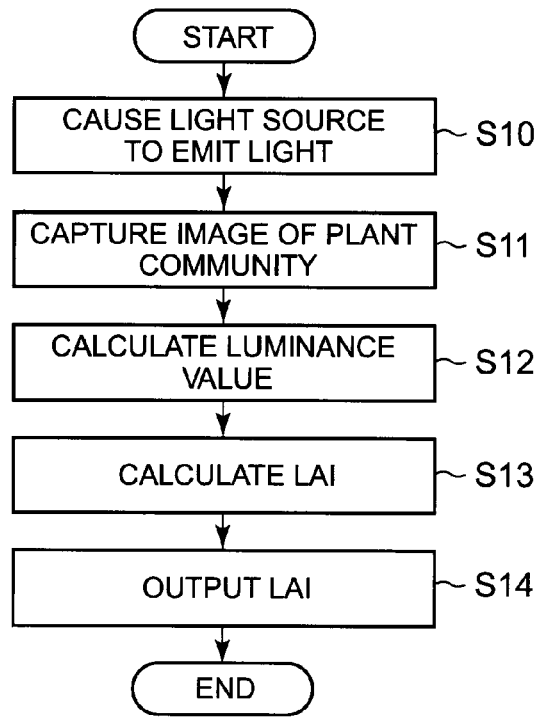
FIG. 3 is a flowchart showing an example of an operation of measuring an LAI using the LAI measurement system.

The following describes an operation of the LAI measurement system. FIG. 3 is a flowchart showing an example of an operation of measuring the LAI using the LAI measurement system. In this exemplary embodiment, the measurement is started in a state where the plurality of light sources 10 are placed in the plant community 30 as shown in FIG. 1, and is repeatedly performed while causing the light sources 10 to emit light in sequence. In this exemplary embodiment, as an example, the measurement is performed while the light source 10 located at the top of the four light sources 10 arranged in the vertical direction is caused to emit light first and then the light sources 10 below are caused to emit light one by one. Note that the order in which the light sources 10 are caused to emit light is not limited to the example in this exemplary embodiment. For instance, the light sources 10 may be caused to emit light in order of increasing height. Moreover, in this exemplary embodiment, the measurement is performed in a nighttime environment or an environment in which sunlight does not enter.

For example, in the case where the camera 20 is placed diagonally above so that the position of each light source 10 can be individually specified in the captured image even when all light sources 10 are caused to emit light simultaneously, the LAI may be measured while causing all light sources 10 to emit light simultaneously.

First, any of the plurality of light sources 10 is caused to emit light (step S10). The camera 20 captures the image in the direction of the plant community 30 in a state where the light source 10 is emitting light (step S11). The LAI measurement device 40 receives the captured image from the camera 20.

Next, the LAI calculation device 40 calculates a luminance value of the captured image received from the camera 20 (step S12). The LAI measurement device 40 transforms the calculated luminance value to illuminance. In this exemplary embodiment, the LAI measurement device 40 extracts the illuminance corresponding to the luminance value calculated in step S12, from the illuminance transformation table stored in the database 42.

The LAI measurement device 40 then calculates the LAI of the location where the light source 10 emitting light is placed, based on the illuminance obtained in step S12 (step S13). In this exemplary embodiment, the LAI measurement device 40 calculates the LAI, by extracting the LAI corresponding to the illuminance from the LAI transformation table stored in the database 42.

Though this exemplary embodiment describes the example of calculating the LAI using the LAI transformation table in which the illuminance and the LAI are associated with each other beforehand, the LAI calculation method is not limited to the example in this exemplary embodiment. For example, the LAI measurement device 40 may calculate the LAI based on the calculated luminance value, without transforming the luminance value of the captured image to the illuminance. In such a case, for example, a table in which the luminance value and the LAI are associated with each other may be prepared beforehand so that the LAI measurement device 40 calculates the LAI by extracting the LAI corresponding to the calculated luminance value from the table.

As an alternative, for example, the LAI measurement device 40 may calculate the LAI by performing an operation using Equation (3) shown below.

$$I/I_0 = e^{-KF} \qquad \text{Equation (3).}$$

In Equation (3), I denotes the intensity of light (which is specifically illuminance, but may also be a luminance value or the like) at a measurement point in the plant community 30. $I_0$ denotes the intensity of light (which is specifically illuminance, but may also be a luminance value or the like) at a reference point (in this example, the position of the light source 10 attached at the top, which is usable as a reference light intensity because there is hardly anything, such as leaves, that blocks light between the light source 10 and the camera 20) in the plant community 30. K denotes an absorption coefficient, which varies depending on plant and, even for the same plant, varies depending on external factors such as weather and time. F is an integral leaf area index.

In this exemplary embodiment, the process of steps S11 to S13 is repeatedly executed for each light source 10 placed in the plant community 30, and the LAI measurement device 40 calculates the LAI at the position of each light source 10.

In the case where the LAI measurement is completed as a result of causing light emission of all light sources 10, the LAI measurement device 40 displays the measured LAI on the display device such as the display (step S14). Here, the LAI measurement device 40 may display the LAI measured at each measurement point. Besides, for example in the case where the light source group is arranged at predetermined intervals in the depth direction (longitudinal direction) and the measurement is performed on such light sources arranged in a lattice, the LAI measurement device 40 may display a graph showing LAI changes with the depth direction as the horizontal axis. Thus, the LAI measurement value can be displayed by various display methods. In addition, the LAI measurement device 40 may, for example, output a file including the measured LAI, or transmit the LAI to another terminal via a network.

As described above, in this exemplary embodiment, the LAI measurement device 40 measures the LAI based on the captured image from the camera 20, without using an expensive illuminometer. Moreover, the LAI measurement device 40 performs the LAI measurement not by using sunlight as a light source but by using the light sources 10. This enables the LAI measurement device 40 to automatically measure the LAI (leaf area index) easily at low cost, without a limit to measurement locations or directions.

In terms of reducing labor in measurement work, a structure in which a plurality of illuminometers are arranged in the vertical direction or the depth direction to measure the LAI might be suggested. However, such a structure requires the use of many expensive illuminometers, which leads to an increase in cost. In this exemplary embodiment, on the other hand, the LAI measurement device 40 is capable of measuring the LAI in the vertical direction or the depth direction all at once simply by processing the image captured by the camera 20, without using an expensive illuminometer. Thus, the LAI measurement device 40 can achieve both a reduction in cost and a reduction in workload for LAI measurement.

If an illuminometer is placed outdoors such as in agricultural land or forests, the illuminometer tends to be stained. This requires workload for maintenance, and increases a possibility of troubles. In this exemplary embodiment, on the other hand, the LAI measurement device 40 can easily perform the measurement merely by arranging many light sources 10. Hence, any workload for maintenance or troubles can be prevented.

Figure 4:
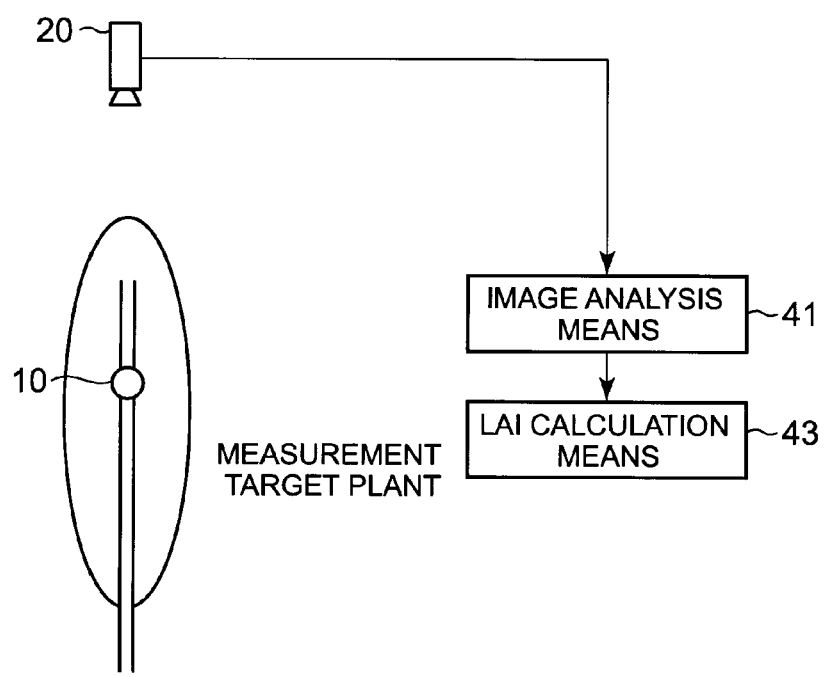
FIG. 4 is a block diagram showing an example of a minimum structure of the LAI measurement system.

The following describes a minimum structure of the LAI (leaf area index) measurement system according to the present invention. FIG. 4 is a block diagram showing an example of the minimum structure of the LAI measurement system. As shown in FIG. 4, the LAI measurement system includes a light source 10, a camera 20, image analysis means 41, and LAI calculation means 43.

The light source 10 is placed in a measurement target plant community. The camera 20 has a function of capturing an image of the measurement target plant community and outputting the captured image. The image analysis means 41 calculates an intensity of light (e.g. illuminance, luminance value) leaking from the plant community when the light source 10 emits light, based on the captured image output from the camera 20. The LAI calculation means 43 has a function of calculating an LAI (leaf area index) based on the intensity of light calculated by the image analysis means 41.

The LAI measurement system having the minimum structure shown in FIG. 4 is capable of automatically measuring a leaf area index easily at low cost, without a limit to measurement locations or directions.

Note that the exemplary embodiment describes above shows characteristic structures of an LAI (leaf area index) measurement system as in the following (1) to (5).

(1) A leaf area index measurement system includes: imaging means (e.g. the camera 20) for capturing an image of a measurement target plant and outputting the captured image; a light source (e.g. the light source 10) placed either on a side of the measurement target plant opposite to the imaging means or at a position of the measurement target plant; intensity calculation means (e.g. realized by the image analysis means 41) for calculating an intensity of light (e.g. illuminance, luminance value) when the light source emits light, based on the captured image output from the imaging means; and leaf area index calculation means (e.g. realized by the LAI calculation means 43) for calculating a leaf area index, based on the intensity of light calculated by the intensity calculation means.

(2) In the leaf area index measurement system, the intensity calculation means may calculate a luminance value of the captured image when the light source emits light, as the intensity of light, wherein the leaf area index calculation means calculates the leaf area index, based on the luminance value calculated by the intensity calculation means as the intensity of light.

(3) In the leaf area index measurement system, the intensity calculation means may calculate illuminance based on a luminance value of the captured image when the light source emits light, as the intensity of light, wherein the leaf area index calculation means calculates the leaf area index, based on the illuminance calculated by the intensity calculation means as the intensity of light.

(4) The leaf area index measurement system may include storage means (e.g. the database 42) for storing the leaf area index in association with the intensity of light, wherein the leaf area index calculation means calculates the leaf area index by extracting, from the storage means, the leaf area index corresponding to the intensity of light calculated by the intensity calculation means.

(5) The leaf area index measurement system may include a plurality of light sources arranged in a vertical direction, wherein the plurality of light sources are individually caused to emit light in predetermined order, and wherein the imaging means captures the image of the measurement target plant each time any of the plurality of light sources emits light, and outputs the captured image.

Though the present invention has been described with reference to the above exemplary embodiment and examples, the present invention is not limited to the above exemplary embodiment and examples. Various changes understandable by those skilled in the art within the scope of the present invention can be made to the structures and details of the present invention.

This application claims priority based on Japanese Patent Application No. 2010-269719 filed on Dec. 2, 2010, the disclosure of which is incorporated herein in its entirety.

INDUSTRIAL APPLICABILITY

The present invention is applicable to measurement of an LAI (leaf area index) in a plant community in agricultural land or forests.

REFERENCE SIGNS LIST

10 light source
20 camera
30 plant community
40 LAI measurement device
41 image analysis means
42 database
43 LAI calculation means
44 LAI output means

The invention claimed is:

1. A leaf area index measurement system comprising: a processor configured to execute an imaging unit for capturing an image of a measurement target plant and outputting the captured image; a light source placed either on a side of the measurement target plant opposite to the imaging unit or at a position of the measurement target plant; an intensity calculation unit for calculating an intensity of light when the light source emits light, based on the captured image output from the imaging unit; and a leaf area index calculation unit for calculating a leaf area index, based on the intensity of light calculated by the intensity calculation unit.

2. The leaf area index measurement system according to claim 1, wherein the intensity calculation unit calculates a luminance value of the captured image when the light source emits light, as the intensity of light, and wherein the leaf area index calculation unit calculates the leaf area index, based on the luminance value calculated by the intensity calculation unit as the intensity of light.

3. The leaf area index measurement system according to claim 1, wherein the intensity calculation unit calculates illuminance based on a luminance value of the captured image when the light source emits light, as the intensity of light, and wherein the leaf area index calculation unit calculates the leaf area index, based on the illuminance calculated by the intensity calculation unit as the intensity of light.

4. The leaf area index measurement system according to claim 1, comprising a storage unit executed by the processor for storing the leaf area index in association with the intensity of light, wherein the leaf area index calculation unit calculates the leaf area index by extracting, from the storage unit, the leaf area index corresponding to the intensity of light calculated by the intensity calculation unit.

5. The leaf area index measurement system according to claim 1, comprising
a plurality of light sources arranged in a vertical direction, wherein the plurality of light sources are individually caused to emit light in predetermined order, and
wherein the imaging unit captures the image of the measurement target plant each time any of the plurality of light sources emits light, and outputs the captured image.

6. A leaf area index measurement device for measuring a leaf area index in a leaf area index measurement system that includes: a processor configured to execute; an imaging unit for capturing an image of a measurement target plant and outputting the captured image; and a light source placed either on a side of the measurement target plant opposite to the imaging unit or at a position of the measurement target plant, the leaf area index measurement device comprising: an intensity calculation unit for calculating an intensity of light when the light source emits light, based on the captured image output from the imaging unit; and a leaf area index calculation unit for calculating a leaf area index, based on the intensity of light calculated by the intensity calculation unit.

7. A leaf area index measurement method comprising: providing imaging unit implemented by a processor for capturing an image of a measurement target plant and outputting the captured image; providing a light source placed either on a side of the measurement target plant opposite to the imaging unit or at a position of the measurement target plant; calculating an intensity of light when the light source emits light, based on the captured image output from the imaging unit; and calculating a leaf area index, based on the calculated intensity of light.

8. A non-transitory computer readable information recording medium storing a leaf area index measurement program for measuring a leaf area index in a leaf area index measurement system that includes: imaging unit for capturing an image of a measurement
target plant and outputting the captured image; and a light source placed either on a side of the measurement target plant opposite to the imaging unit or at a position of the measurement target plant, the leaf area index measurement program causing a computer to execute:
an intensity calculation process of calculating an intensity of light when the light source emits light, based on the captured image output from the imaging me-a~ unit; and
a leaf area index calculation process of calculating a leaf area index, based on the calculated intensity of light.

* * * * *